(12) United States Patent
Meisegeier et al.

(10) Patent No.: US 7,658,825 B2
(45) Date of Patent: Feb. 9, 2010

(54) MEASURING DEVICE AND MEASURING METHOD FOR DETECTING ANALYTES

(75) Inventors: Bernhard Meisegeier, Veitshochheim (DE); Detlev Zwingmann, Marburg (DE); Jurgen Oberstrass, Habichtswald (DE); Reinhard Schaper, Korbach (DE)

(73) Assignee: Analyticon Biotechnologies AG, Lichtenfels (DE)

( * ) Notice: Subject to any disclaimer, the term of this patent is extended or adjusted under 35 U.S.C. 154(b) by 785 days.

(21) Appl. No.: 11/219,833

(22) Filed: Sep. 7, 2005

(65) Prior Publication Data

US 2006/0076249 A1 Apr. 13, 2006

(30) Foreign Application Priority Data

Sep. 9, 2004 (EP) .................................. 04021433

(51) Int. Cl.
*C12Q 1/00* (2006.01)
*G01N 31/22* (2006.01)
*G01N 27/26* (2006.01)
*G01N 15/06* (2006.01)
(52) U.S. Cl. ............................. 204/403.01; 204/403.04; 204/403.09; 204/400; 422/56; 422/57; 422/68.1
(58) Field of Classification Search ................. 204/400, 204/403.01, 403.04, 403.09, 403.1, 193, 204/280; 422/56, 57, 58, 61, 68.1
See application file for complete search history.

(56) References Cited

U.S. PATENT DOCUMENTS

| 4,368,323 | A | * | 1/1983 | James | 536/56 |
| 6,027,692 | A | * | 2/2000 | Galen et al. | 422/82.05 |
| 6,197,494 | B1 | | 3/2001 | Oberhardt | |
| 6,299,757 | B1 | * | 10/2001 | Feldman et al. | 205/775 |
| 6,576,102 | B1 | * | 6/2003 | Rappin et al. | 204/403.14 |
| 6,649,679 | B1 | * | 11/2003 | Stockl et al. | 524/253 |
| 6,670,115 | B1 | * | 12/2003 | Zhang | 435/5 |
| 6,766,817 | B2 | | 7/2004 | da Silva | |
| 2002/0182600 | A1 | * | 12/2002 | Smith | 435/6 |
| 2003/0180815 | A1 | | 9/2003 | Rawson et al. | |
| 2004/0106190 | A1 | | 6/2004 | Yang et al. | |

FOREIGN PATENT DOCUMENTS

| CA | 2223705 | * | 8/1999 |
| DE | 100 32 042 A1 | | 1/2002 |
| EP | 0 170 375 B1 | | 2/1986 |
| GB | 2 391 068 A | | 1/2004 |
| WO | WO 99/58709 | | 11/1999 |
| WO | WO 00/70327 | | 11/2000 |

* cited by examiner

*Primary Examiner*—Nam X Nguyen
*Assistant Examiner*—Gurpreet Kaur
(74) *Attorney, Agent, or Firm*—Clark & Brody (57) ABSTRACT

A measuring device for the detection and determination of the concentration of at least one analyte in a liquid medium consists of a polymeric carrier having biologically active specific binding molecules dried on its upstream portion. A multiple electrode set consisting of at least one reference electrode and at least one working electrode is located thereon in a downstream region. The working electrode is provided with biologically active specific binding molecules. The carrier has a sample application zone, which is adjoined, in the downstream direction, by a non-deformable, through-flow reaction and detection chamber, a variably dimensioned interstice, and a liquid absorption element. For a qualitative and quantitative analyte determination, two liquid media are applied in succession to the sample application zone. While the first can contain the wanted analyte, the second provides for the formation of an electrical signal.

41 Claims, 2 Drawing Sheets

MEASURING DEVICE AND MEASURING METHOD FOR DETECTING ANALYTES

FIELD OF THE INVENTION

The invention relates to a measuring device for the detection and/or determination of at least one analyte dissolved in a liquid medium, to a method for the production of the measuring device, to a method for its operation and to the use of the measuring device.

BACKGROUND OF THE INVENTION

Sensors for the determination of analytes in a sample solution are known in the prior art. Thus, in DE-A1-100 32 042, a system comprising a working electrode and a counter-electrode has been applied to a plastic carrier material. The working electrode is constructed of a number of layers, namely of at least one reaction layer and one protective layer. The protective layer is necessary because electrochemical signals in a sample solution are transferred to a sublimable mediator and thence to the working electrode. Without the protective layer, the mediator would sublime off and the sensor would be impaired in its function. The multilayer arrangement, however, makes it difficult to bring an exactly defined amount of sample or substrate solution into contact with the working electrode, which can lead to measuring inaccuracies. Moreover, the measurement requires a number of washing steps and prolongs the measuring time.

In WO-A1-99/58709, a testing device is described which consists of a carrier, an electrode system lying thereon and consisting of three electrodes of different dimensions and a number of net-like fabrics and covering layers deposited thereon. These layers and fabrics insulate the individual electrodes from one another. Moreover, they ensure that a measuring sample applied through an opening in the uppermost layer will be distributed through the flexible stack of layers around the electrodes more or less satisfactorily. However, the elastic stack will not absorb liquid samples applied in succession in exactly the same manner and disperse them between the individual layers in the same way every time. Therefore a constant amount of measuring sample cannot be caused to surround the electrodes in a defined volume range. As a result, measuring errors can occur and measurements show poor reproducibility. In other respects, the sandwich-like stack arrangement described is complicated to produce.

The testing device described in EP-B1-0 170 375 overcomes the disadvantages of a flexible construction. It discloses a measuring cell consisting of two plate-like hard plastic surfaces. These are arranged at a close distance from one another and enclose a particle-selective electrode system between them. The distance between the two surfaces from one another is set by ridges which run along the longitudinal sides of the surfaces. One of the two plastic surfaces is of larger construction than the other and forms a lip to which an analysis solution can be applied. Driven by capillary forces, this solution flows as far as the electrode system and at the same time causes air situated in front of it to be displaced in the downstream direction and thus to leave the testing device. Accordingly, analysis solution will flow into the testing device until the latter is completely filled with liquid. It is not possible to introduce further liquid, for example for washing purposes, into the interior of the testing device without beforehand laboriously having to remove the volume of solution already enclosed between the two plates by means of an absorbent fleece or fabric.

WO-A1-00/70327 also cannot completely overcome the aforementioned disadvantages. It discloses a testing apparatus for the quantitative electrochemical analysis of an analyte in a solid phase. It consists of a layer which contains electrodes and on which a supporting layer having a hole is disposed. The hole lies directly on top of the electrodes. A chromatographic test strip lies on the supporting layer. This is divided into three sections and consists of a sample collection pad adjoined by a flow surface, designated as a membrane, and an absorption pad. The sample collection pad contains a soluble substance specific to an analyte said substance carrying a label.

BRIEF SUMMARY OF THE INVENTION

In a first step, a liquid sample is applied to the sample collection pad. A major portion of the sample liquid flows through the membrane into the absorption pad. Only a small portion reaches the hole above the electrodes. This can therefore only be filled completely with liquid in the case of large sample volumes. If the anaylte sought is present in the sample flowing downstream, it will form a complex with the specific substance. This migrates further downstream and binds to a further specific substance immobilized on the membrane in the region of the hole. A sandwich compound results, the amount of which can only be electrochemically detected if the membrane and the electrodes are in liquid contact with one another via the hole.

In a second step, a substrate solution is applied either to the sample collection pad or directly to the membrane above the hole so that the latter, depending on the amount applied, fills more or less completely with liquid. This mixes with the sample solution already present in the hole. It is thus not possible to place in the hole a defined amount of a single solution which, moreover, is free from traces of the respective other solution. Furthermore, it is not possible to replace the sample solution completely by the substrate solution. This can lead to measuring inaccuracies and non-reproducible results of measurement, especially if the sample solution contains electroactive constituents which are not present in the substrate solution. The prior art testing apparatus, which consists of many individual parts, is complicated in its architecture and thus expensive to produce.

It is an object of the present invention to overcome the drawbacks of the prior art by providing a measuring device and method for the detection of analyte concentrations in liquid media accurately and rapidly. In this method, electroactive impurities in a measuring sample should influence the measured result just as little as different volumes of the liquids used. The measuring device should, with low use of material, be inexpensive and simple to produce and in addition be, even after relatively long storage, so robust mechanically and chemically that it yields precise and reproducible readings.

In a device for the detection and/or determination of the concentration of at least one analyte present in a liquid medium, consisting of a strip-shaped carrier having two longitudinal edges, to which carrier a printed multiple electrode set consisting of at least one reference electrode and of a least one working electrode has been applied, and of ligands which are suitable for binding a biologically active specific binding molecule or the analyte, the invention proposes that the device comprises a rigid reaction and detection chamber, adapted for continous flow of the medium along the strip-shaped carrier, said reaction and detection chamber being formed by an elongated support applied to said longitudinal edges of said carrier having a cover disposed on said support and that a liquid absorption element is disposed downstream of said reaction and detection chamber. Measuring solutions can be applied in different amounts to the carrier in order to flow through the same in the direction of the liquid absorption element. However, irrespective of the starting volume, a constant amount of solution will always remain in the reaction and detection chamber, which is why very precise measurements can be realized. Moreover, traces of solution from the reaction and detection chamber can be rinsed out using a second solution. Even then, exactly the same amount of liquid remains in the reaction and detection chamber. Therefore, analyte concentrations can still be determined very precisely even if a number of solutions have to be employed in succession to carry out a measurement.

The carrier is designed as a self-supporting flow surface for the liquid medium. It is a single piece and consists of a polymeric, nonconducting, preferably rectangular material. These embodiments of the carrier decrease the production costs and reduce the weight of the measuring device. If selected molecules are required to bind on the surface of the carrier, ligands and/or biologically active specific binding molecules are applied thereto. It is also possible to immobilize some or all of them on the carrier whereby space is gained on the electrodes in order to fix yet other molecules to their surfaces.

If carrier materials are used which are very sluggish to react or have no ability to bind biologically active specific binding molecules, the surface of said materials must be prepared for the ligands to be applied thereto. Therefore, it is proposed to equip the carrier with a primary coating which consists of proteins selected from the group consisting of the animal or human albumins and/or from the group consisting of the globulins and/or from the group consisting of the glycoproteins. Polypeptides, for example polyamino acids and/or degradation products of proteins, which preferably originate from the supportive and connective tissue, can be utilized for this purpose.

In the measuring device a sample application zone is formed at one end of the carrier. This is the only place where a sample to be measured can be fed to the measuring device. The zone or at least a part thereof must be treated with surface-active substances and that it must have the ability to absorb the liquid medium. An even greater improvement in sample absorption is achieved by placing a mesh-like or porous material, preferably treated with surface-active substances, in the sample application zone.

For providing electrical supply potential in the measuring device, each working electrode and each reference electrode is connected conductively to an assigned conducting track and each conducting track is connected conductively to a contact which can in turn be connected to an electrical measuring apparatus.

The material used for at least one of these electrodes and for their respectively assigned conductive tracks and their respectively assigned contacts is gold, silver, platinum, nickel, palladium, titanium, copper or carbon. It is particularly convenient if at least one of the electrodes consists of a dried graphite paste or is an electrode which can be prepared from metal pastes and/or metal salt pastes by drying. Electrode pastes of this type can be distributed on the carrier in any desired form and thus make it possible to achieve almost any electrode geometry.

In a further embodiment of the invention, at least one working electrode carries ligands and/or biologically active specific binding molecules, for example on its surface. If such particles are applied directly to the electrode, electroactive substrate forms immediately result on the electrode surface and a rapid signal transmission occurs. The electrode coating can additionally be supplemented if reaction-nonspecific binding molecules are disposed and/or immobilized on at least one further working electrode. Particles of this type record changes in the measuring solution which are not formed by a specific electroactive substrate and accordingly ensure that measuring errors do not occur.

The ligands are applied as a solution having a concentration of from 0.0007 to 0.7 mol/l and preferably from 0.035 to 0.35 mol/l. They consist of different classes of compounds significant to the invention. Thus they are formed from ribonucleic acids or deoxyribonucleic acids or they consist of amino-carboxylic acids, preferably diaminocarboxylic acids. According to claim 19, non-monomeric homodet or heterodet amino-carboxylic acids of the composition R—$CH(NH_2)$—$(CH_2)_n$—COOH linked in peptide-like manner, for example polyaminocarboxylic acids, are particularly important, where R stands for a proton or preferably for an amino, imino, hydroxyl, thiol, hydroxyalkyl, aminoalkyl, or carboxyalkyl group and n assumes a value of from 0 to 6, preferably 0.

Other ligands which can be used are proteides or proteins which have preferably been isolated from the bacterium *Streptomyces avidinii*. At least one ligand can be a phenylboronic acid, for example for the detection of HbA1c.

The biologically active specific binding molecules are responsible, as can be inferred from their name, for creating a linkage with surfaces, ligands, and analytes, which is necessary for the invention. For this purpose, they have binding sites for at least one ligand or are bound thereto. Moreover, they have at least one specific binding site for binding an analyte.

One or more catalytically active proteins are preferably covalently bonded to the biologically active specific binding molecules and/or the ligands. By means of this essential feature of the invention, an analyte-binding molecule can simultaneously convert a substrate molecule into an electroactive form.

In order to ensure that the reaction and detection chamber has a constant volume, which is essential to the invention, its constituents must be defined. Therefore the elongated support is divided in two and is permanently adhesively attached, in the form of two strips, to the two longitudinal edges of the carrier. Said strips consist of a polymer material and/or of a melt adhesive and possess the same thickness as the liquid absorption element. The invention is significantly developed because this defines that the strips rest on only a portion of the two longitudinal edges of the carrier, an interstice being formed between the strips and the liquid absorption element, from which interstice the strips extend in the upstream direction on the longitudinal edges. This interstice contributes to the fact, and/or ensures, that on each application of liquid to the carrier a defined amount of sample remains in the reaction and detection chamber.

The cover helps create the constant volume of the reaction and detection chamber. It consists of a polymeric, preferably rectangular, material and is connected to the elongated support in such a way that it covers the carrier and also the multiple electrode set and the liquid absorption element. Alternatively, it can also cover only one or more parts of the carrier.

The cover includes on its upstream side, at least one slot-shaped and/or semicircular or polygonal recess and/or opening, which is arranged in such a way that the sample application zone of the carrier can be charged with liquid medium. In one embodiment of the novel device the liquid absorption element is fixed adhesively to that side of the cover which faces the carrier.

The surface characteristics of the cover can be significantly refined and improved. The cover, or at least part of it, is to this end treated with surface-active substances and thereby imparted with a hydrophilic and/or hydrophobic surface. In a variant, that side of the cover which faces the carrier possesses hydrophilic surface properties, in the region of the multiple electrode set and in particular above the working electrode(s) and above the reference electrode, and has, at least in part, a hydrophobic surface in the region of the sample application zone.

The reaction and detection chamber is open in the downstream and upstream directions and the interstice borders on its downstream end. Thus, on the one hand, a continuous liquid stream will pass through the carrier, and, on the other hand, the configuration is such that it assists, or ensures, the provision of a constant capacity for liquid in the reaction and detection chamber.

The liquid absorption element is indispensable to the invention, because its sucking action improves the flow of a measuring solution in the downstream direction. For this purpose, it is disposed on the carrier at a distance from the sample application zone downstream thereof and covers the conducting tracks in that it bears firmly against them, for example.

In order to absorb the liquid medium particularly well, the liquid absorption element consists of an absorbent porous fibrillar material and is fixed to the carrier by adhesion. It is constructed from at least one fiber layer or from at least one fabric, which consists of cellulose fibers or glass fibers or mixtures thereof or is composed of organic polymers. A practical continuation of the idea of the invention provides for the liquid absorption element to be treated with surface-active substances, preferably with those which have hydrophilic properties. This increases the tendency of the liquid medium to flow rapidly downstream.

Surface-active compounds according to the invention comprise substances which contain hydrophilic groups, for example —COOMe, —OSO$_3$Me, —SO$_3$Me, —NH$_2$, =NH, —NR$_3^+$ and hydrophobic alkyl chains having from 10 to 18 carbons or alkylaryl groups. Preferably, substances having the empirical formula $C_{20}H_{37}NaO_7S$ or $C_{18}H_{29}NO_3S$ are used.

In order to impart to the device according to the invention the necessary rigidity in conjunction with low weight, the use of polymers is appropriate. In this case it is particularly convenient if the polymeric material is a polyethylene, a polystyrene, a polyurethane, a polyvinyl acetate, a polyester, for example polyethylene terephthalate, an epoxy resin, a methacrylic polymer, a polycarbonate, a polyvinyl chloride or a copolymer of said compounds. Excess material consumption is avoided if the polymeric material is a foil preferably manufactured from polyester, polycarbonate, or polyvinyl chloride.

Another aspect of the invention includes a method for the production of a device for the detection and determination of the concentration of at least one analyte dissolved in a liquid medium. According to the invention, this is achieved by processing an electrode material to give a paste, which is applied to a carrier in such a way that a multiple electrode set is formed consisting of at least one working electrode and at least one reference electrode and conducting tracks and contacts attached thereto. The carrier provided with the multiple electrode set is then dried at an elevated temperature, and subsequently ligands and/or biologically active specific binding molecules and/or catalytically active proteins are applied to it. This takes place in the region of the multiple electrode set or in a region which is disposed upstream of the multiple electrode set. An elongated support, a cover and a liquid absorption element are fixed to the carrier thus obtained such that the cover and the carrier are spaced from one another. A measuring device produced in this manner is such that a solution can flow therethrough and during said flow a certain volume of solution can simultaneously be retained in the region of the electrodes. Moreover, analytes which are specific to biologically active binding molecules or ligands can now be accurately determined. They are selectively separated off from the measuring solution and bound to the carrier on or close to the electrodes. Finally, the use of conducting pastes makes it possible to produce electrodes and conducting tracks and contacts in a wide variety of shapes, sizes, and configurations.

It is important for the invention that at least one working electrode is provided with specific molecules. This takes place in that the paste contains ligands and/or biologically active specific binding molecules and/or catalytically active proteins and is applied by means of a screen printing technique. This procedure is timesaving, since subsequent coating of the working electrode is unnecessary. However, it is only practicable if the ligands or the biologically active specific binding molecules and the catalytically active proteins are temperature-resistant and are not destroyed during the drying process. Since this, however, does not apply to all molecules employed, a supplementary procedure is carried out. This specifies that at least one of the dried electrodes is coated with ligands and/or biologically active specific binding molecules and/or catalytically active proteins, preferably with the aid of crosslinking molecules or coupling reagents. In the same manner, at least one of the dried electrodes is coated with ligands and/or reaction-nonspecific binding molecules, preferably with the aid of crosslinking molecules or coupling reagents.

The measuring sample flows more rapidly along the carrier if regions of the measuring device disposed downstream are rendered hydrophilic. Therefore the liquid absorption element is treated with a solution of a surface-active substance and dried, this substance in a preferred embodiment being a compound of the empirical formula $C_{20}H_{37}NaO_7S$ or $C_{18}H_{29}NO_3S$, employed in a concentration of from 0.001 to 5% w/v, preferably from 0.1 to 3% w/v.

A further aspect of the invention involves a method for the detection and determination of the concentration of at least one analyte dissolved in a liquid medium using a device which consists of at least one working electrode and at least one reference electrode. According to the invention, a definable amount of the liquid medium is applied to a sample application zone of the device. A specifiable period of time is then allowed to elapse in order to allow interaction of the analyte(s) with ligands and/or biologically active specific binding molecules and/or catalytically active proteins to take place. Then, a solution is applied to the sample application zone which contains at least one reaction-specific substrate for a catalytically active protein or for a number of catalytically active proteins and the device is connected to an electrical measuring apparatus. After an incubation time, an electrical signal is read off on the measuring apparatus connected to the device for each analyte to be determined and a corresponding concentration of the respective analyte is assigned to it with the aid of a calibration curve. Only two solutions are necessary for a measurement, and an analyte determination can thus be carried out simply and quickly. Because wash liquids are not needed, the process is very user-friendly.

The process according to the invention is quick and little liquid medium is needed. Thus the amount to be defined ranges from 0.01 to 20 µl and preferably from 1 to 10 µl. The period of time to be predetermined is between 5 and 600 seconds, preferably between 10 and 120 seconds and more preferably between 20 and 60 seconds. The low consumption of liquid is also shown by the amounts of specific substrate defined in claim 50. Only amounts between 0.1 μl and 500 μl, preferably between 1 μl and 100 μl, and more preferably between 10 μl and 30 μl, of this solution must be pipetted onto the sample application zone. The incubation time subsequent thereto lies, according to claim 51, in a range of from 2 to 100 seconds, preferably from 5 to 30 seconds and is more preferably 20 seconds, and is thus likewise very short.

The accuracy of the analyte determination can be markedly improved, in particular, in solutions containing many electroactive particles. For this purpose, the electrical signal read off is compared with a further electrical signal which originates from a second, nonspecific working electrode, this second working electrode being provided with only reaction-nonspecific ligands or binding molecules.

The device is used for the detection and for the determination of the concentration of at least one analyte from body fluids such as whole blood, plasma, serum, urine, secretion, cerebrospinal fluid, from extracts of body tissues and from smear or swab material.

Further features, details and advantages of the invention follow from the wording of the claims and from the following description of exemplary embodiments with reference to the drawings, in which:

DETAILED DESCRIPTION OF THE INVENTION

Figure 1:
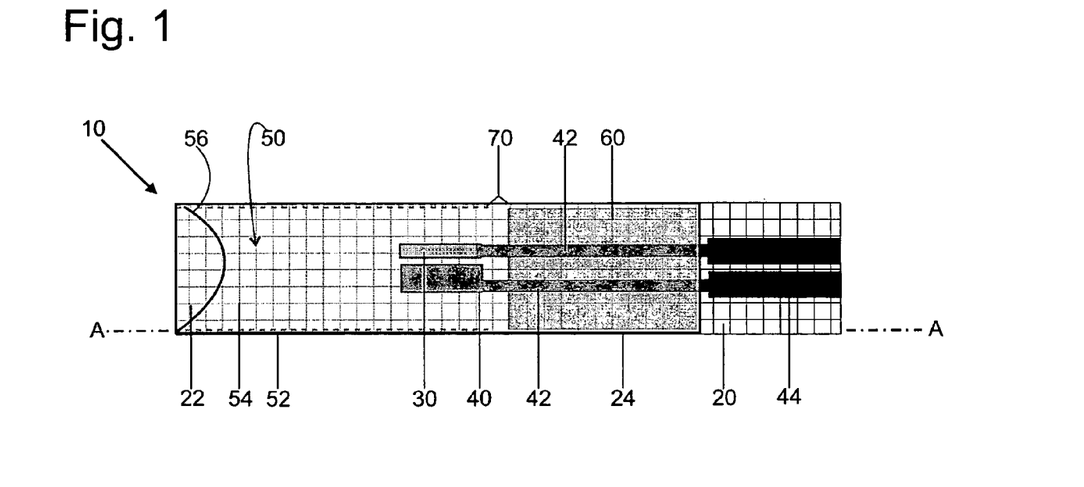
FIG. 1 is a top view of a measuring device consisting of a reference electrode and a working electrode.

The measuring device generally designated in FIG. 1 by the reference numeral 10 is used for the qualitative and quantitative determination of dissolved analytes. It consists of a carrier 20, to which, in a basic design, a set of electrodes consisting of a working electrode 40 and a reference electrode 30 has been applied. Electrodes 30, 40 are disposed in a reaction and detection chamber 50. This consists of part of carrier 20, an elongated support 52, and a cover 54. It is open at both ends. Cover 54 has on one of these open ends a recess 56, which provides a sample application zone 22 on carrier 20. On the other end of cover 54, there is a space 70 which is in turn confined by a liquid absorption element 60.

In the reaction and detection chamber 50, biologically active specific binding molecules are present, which can interact with a sought-after analyte and in some cases carry at least one catalytically active protein.

To determine the concentration of the analyte, a measuring sample is applied to thr sample application zone 22. Through capillary action the sample migrates downstream into the reaction and detection chamber 50. The analyte reacts there with a biologically active specific binding molecule carrying a catalytically active protein. A complex is formed which moves further downstream as far as electrodes 30, 40, where it interacts with an immobilized, biologically active specific binding molecule. In this way, the sought after analyte molecules are concentrated near to, or on, at least one electrode 40.

The remaining measuring sample is dispersed further downstream into interstice 70 and is partially absorbed by the adjacent liquid absorption element 60. In a second step, a solution is applied to sample application zone 22, which contains at least one reaction-specific substrate for at least one catalytically active protein. This likewise penetrates into reaction and detection chamber 50 and displaces unbound constituents of the measuring sample into interstice 70 and liquid absorption element 60. The substrate reacts with the catalytically active protein. Catalytically active proteins only remain in reaction and detection chamber 50 if the biologically active specific binding molecule bound thereto interacts with the analyte by binding and this is in turn captured by the immobilized biologically active specific binding molecule. Therefore, the amount of converted reaction-specific substrate is proportional to the concentration of catalytically active protein in reaction and detection chamber 50 and is thus a measure of the amount of sought after analyte in the measuring sample.

The catalytically active protein converts the associated reaction-specific substrate into an oxidized or reduced, in any case electroactive, substrate form. This interacts with working electrode 40, whereby an electrical signal is produced in the form of a current and/or voltage change. This is proportional to the amount of electroactive substrate form produced and is thus a quantitative measure of the amount of analyte in a measuring solution. In order to obtain reproducible readings, it is necessary that a constant measuring volume be always present in the reaction and detection chamber 50. This is ensured or at least assisted by the provision of interstice 70 between the liquid absorption element 60 and the reaction and detection chamber 50.

Carrier 20 of measuring device 10 consists of a flexible, preferably self-supporting and nonconducting layer of plastics material. This is a single piece and is produced from a polymer or a copolymer of two or more of the polymeric materials mentioned below. In a particular development, it possesses a microscopic surface structure through which, in addition to liquids and small antigens, dissolved biological macromolecules such as, for example, enzymes, globular proteins, nucleic acids, infectious agents and antibodies can also easily diffuse. Carrier 20, preferably in foil form and of rectangular design, possesses two longitudinal edges 24 and is so thick that it can be incorporated in a measuring device 10 without an additional supportive layer, for example between 0.1 mm and 5 mm. However, it can also be of irregular design in the longitudinal direction and have regions of wider dimensions. Moreover, the plastic layer can taper and/or be rounded in one direction.

In order to be able to selectively bind biologically active specific binding molecules at certain sites, such as the reaction and detection chamber 50, to a low-activity plastic layer, a coating is previously applied to carrier 20. For this purpose it is treated, as it were, as a primer with a solution whose constituents bind to its surface electrostatically or by means of van der Waals forces. For example, polyamino-carboxylic acids modify, a polyethylene foil chemically in such a way that it can covalently bind biologically active specific binding molecules.

For surface activation, there are used in addition to the acids mentioned, however, protein solutions of animal or human albumins, globulins or glycoproteins, and preparations from bacterial proteins. Examples of albumins are lactalbumin and human serum albumin, and serum albumins from cattle, rabbits, sheep, horses, pigs, and goats. The glycoprotein employed is, for example, ovomucoid and the bacterial proteins used are preferably isolated from *Streptomyces avidinii*. In addition to proteins, however, proteides are used, that is to say, proteins which are provided with further groups, for example with carbohydrate, nucleic acid, or lipid groups.

In addition, polyamino acids or polypeptides are used, the latter preferably being degradation products of proteins of the supportive and connective tissue, such as, for example, Gelafusal® obtained from gelatin.

A particularly good adhesive base is achieved if the proteins, proteides, polyamino acids, or polypeptides used are arranged on the carrier 20 as a result of denaturation in a "random coil" conformation. For this purpose, a solution of these is heated, prior to application, at from 50° to 80° C., or chaotropic agents such as urea or guanidine salts are added to the solution. The same is achieved by changing the pH, by means of ultrasound, mixing with organic solvents, or by treatment with ionizing radiation.

Sample application zone 22 situated at the upstream end of carrier 20 consists, in a basic design, only of an open semicircular carrier subregion. It is designed such that a measuring sample can be pipetted on or dripped on effortlessly. In a development (not shown), however, it is made up of a number of regions separated from one another, whose appearance is specified by the shape of recess 56 or by additional stamped-out areas (not shown) in cover 54.

In order that the measuring sample flows into reaction and detection chamber 50 as quickly as possible, sample application zone 22 is treated with surface-active compounds such as, for example, detergents. If these are applied such that their hydrophilic character increases in the downstream direction, a particularly high inflow velocity is achieved. In a further development, a mesh-like material (not shown), for example a nylon fabric treated with detergents, lies on sample application zone 22 and splits up a measuring drop to be investigated. If a number of such net fabrics are placed one over the other, this additionally promotes the uniform distribution of a measuring sample on the sample application zone 22 and thus cause a rapid inflow. This effect is particularly marked if the individual fabrics have mesh widths of different size and are superimposed on each other, beginning with the smallest mesh width.

In the downstream region of the coated carrier 20 there are disposed means for deriving electrical signals, which means are insulated from each other in one embodiment (not shown). They consist of electrodes 30, 40, each of these being connected via its own conducting track 42 to a contact 44 disposed at the downstream end of carrier 20.

Each electrode 30, 40 is wider than the slender and long conducting tracks 42, so that a maximum surface area is available for interactions with dissolved substances of a measuring solution. According to FIG. 1, all electrodes 30, 40 possess a rectangular shape. In a development, however, they can be square, circular, semicircular with the semicircle closed or open on the upstream side thereof, or polygonal. Generally, each electrode 30, 40 takes up a surface area of from 0.2 to 20 mm$^2$, preferably from 1 to 5 mm$^2$, the working electrode 40 as a rule occupying more area than reference electrode 30. In FIG. 1, it is seen that the working electrode 40 needs approximately three times more space.

All parts 30, 40, 42, 44 intended to conduct an electric current and/or voltage consist of carbon—preferably graphite—or of silver, platinum, gold, palladium, titanium, nickel, or copper. If the starting substances are present as a powder or paste, they are, if possible, applied to carrier 20 in one step by means of screen printing. In another embodiment, a component of flat metallic material comprising an electrode 30, 40 with associated conducting track 42 and its contact 44 is produced and affixed by adhesion.

Reference electrode 30 is not provided with particle-selective groups or compounds. It is built as an Ag/AgCl electrode. For certain applications, however, it consists of at least one carbon modification and/or of the elements mentioned above, which can be used both individually and in combination with each other. All conducting tracks 42 and contacts 44 are produced using a carbon-containing graphite paste (e.g. Ercon E0455-125 graphite ink).

Working electrode 40 is preferably manufactured from graphite paste and possesses on its surface immobilized ligands or immobilized ligands to which biologically active specific binding molecules are bound. In one embodiment, it additionally carries immobilized catalytically active proteins, which are either present directly on its surface and/or are bound to ligands or to biologically active specific binding molecules. The components: working electrode 40, ligand, biologically active specific binding molecules, and catalytically active protein, are bound to one another covalently, electrostatically, by means of hydrogen bonds or by van der Waals forces.

In a refined embodiment, two catalytically active proteins of different specificity are bound permanently to the surface of working electrode 40. In one form of this embodiment, the first protein is bound to a ligand or to a biologically active, specific binding molecule, while the second is immobilized directly on the surface of working electrode 40. Both of these two-protein arrangements are convenient if the analyte to be determined is a reaction-specific substrate. Each substrate reaching working electrode 40 is converted by the first catalytically active protein to an intermediate, which reacts with the second catalytically active protein (reaction cascade). During this process, the electroactive substrate form results, the amount of which is indicated by the size of the electrical signal generated on working electrode 40 and represents the amounts of the analyte in the measuring sample.

In yet another development, working electrode 40 carries a ligand or a ligand having a biologically active specific binding molecule and, furthermore, exclusively the second catalytically active protein. This is directly bound to working electrode 40 or else to the ligand or the biologically active specific binding molecule and again serves to form the electroactive substrate form in a reaction cascade, the first catalytically active protein being situated on the carrier 20.

For the determination of a single analyte, that is, for the creation of a monoanalyte sensor according to FIG. 1, at least one working electrode 40 and at least one reference electrode 30 are necessary.

Particle-selective groups or compounds, that is to say, ligands, biologically active specific binding molecules, and/or catalytically active proteins can, individually or linked together, not only be bound to working electrode 40, but also be disposed in various regions on carrier 20. This arrangement is based on covalent interaction, electrostatic interaction, interaction produced by means of hydrogen bridges or else on interaction caused by van der Waals forces, with the plastic layer. It ensures that particle-selective groups or compounds are dried onto the carrier 20 and are therefore mobile in the moist state, and/or are permanently fixed to the carrier and are therefore immobile in the moist state.

Ligands have two functions. Either they directly bind a certain analyte to themselves or they serve as a bridging member between the carrier surface or working electrode surface on the one hand and biologically active specific binding molecule on the other hand.

In one embodiment of the invention, the measuring device 10 is treated with a solution which contains ligands in concentrations of from 0.0007 to 0.7 mol/l and preferably from 0.035 to 0.35 mol/l. The compound involved is one selected from the family consisting of the amino-carboxylic acids, in particular the diaminocarboxylic acids.

Non-monomeric homodet-(=exclusively via peptide bonds) or heterodet-(=not exclusively via peptide bonds) linked polyaminocarboxylic acids are equally suitable. They have the general structural formula R—CH(NH$_2$)—(CH$_2$)$_n$—COOH, where R comprises a proton and an amino, imino, hydroxyl, thiol, hydroxyalkyl, aminoalkyl or carboxyalkyl group and n assumes a value of from 0 to 6, preferably 0.

Sources of relatively high molecular weight compounds linked in a peptide-like manner are depolymerized hydrolysis products of fibrillar scleroproteins of animal connective tissue. An example thereof is Gelafusal®, obtained from collagen by oxidative/thermal degradation processes. If proteins are to be employed as ligands, they are obtained, inter alia, from the bacterium *Streptomyces avidinii*.

Furthermore, ribonucleic acids or deoxyribonucleic acids and various boronic acids such as, for example, phenylboronic acid can be used as a ligand.

Carbohydrate-based compounds, such as, for example, concanavalin A, various lectins or agglutinins, such as hemagglutinin, and streptavidin, can be employed as ligands.

One embodiment of the measuring device proposes polymeric amino-carboxylic acids as immobilized ligands on the entire carrier 20. In the immediate vicinity of a working electrode 40, or on it, biologically active specific binding molecules are covalently bonded to the ligands and are therefore immobile. In the region of, or beyond the sample application zone 22, i.e. upstream of the electrodes 30, 40, there are situated biologically active specific binding molecules which are mobile in the moist state and which carry a catalytically active protein. The sought after analyte from the measuring sample binds to one of the mobile binding molecules and a mobile complex formed thereby diffuses as a result of capillary action into reaction and detection chamber 50, where it will bind to one of the covalently bonded binding molecules.

In another embodiment, carrier 20 is free of ligands or contains them only in distinct regions. The mobile complex consists of a biologically active specific binding molecule and a catalytically active protein, and, optionally, a mobile ligand. After absorption of the analyte, this complex migrates as a result of capillary action on carrier 20 into reaction and detection chamber 50, where it binds to an immobilized ligand or to an immobilized biologically active specific binding molecule. This can likewise be linked to a ligand.

To preserve the biological and immunological activity of the biologically active specific binding molecules and the catalytically active proteins, these are embedded on carrier 20 in polyhydroxy compounds or polymeric amino-carboxylic acids or better in a mixture thereof. Long-term stability, which is demanded for commercial products, is thereby attained.

Biologically active specific binding molecules are able to bind an analyte selectively to themselves. Depending on their usage, they are linked to a catalytically active protein and/or to a ligand. They can be permanently fixed to carrier 20 or else applied so that they are immobile in the dry state and on moistening move forward along carrier 20. They can also be bound undetachably to a ligand which is already immobilized on carrier 20.

Often, two biologically active specific binding molecules are used, of which one is mobile upstream on carrier 20 and is covalently linked to a catalytically active protein to give a conjugate, while the second is permanently adherent in the downstream region in the vicinity of working electrode 40 or is immobilized on it. It is thus ensured that the analyte and conjugate diffuse in an appropriate proportions to the vicinity of working electrode 40 or onto it, where they are permanently retained. A sandwich of conjugate, analyte and immobilized biologically active specific binding molecule is formed.

The group of biologically active specific binding molecules can include all compounds which selectively bind an analyte or an antigen or their hapten component(s) without, however, chemically reacting with them. Among these, in particular, are included monoclonal and polyclonal antibodies and antigens.

The catalytically active proteins employed are usually enzymes or recombinants of antibodies and enzymes. Thus oxidoreductases, in particular glucose dehydrogenase, glucose oxidase and peroxidase are preferably used, but other enzymes are equally suitable.

In order to conserve the compounds mentioned on carrier 20 in a native conformation, dissolved polyhydroxy compounds, for example mono-, oligo- or polysaccharides, can be added. The native structure can also be conserved using a solution of proteins and hydroxy compounds. This is also used, however, for activating the carrier 20.

Figure 2:
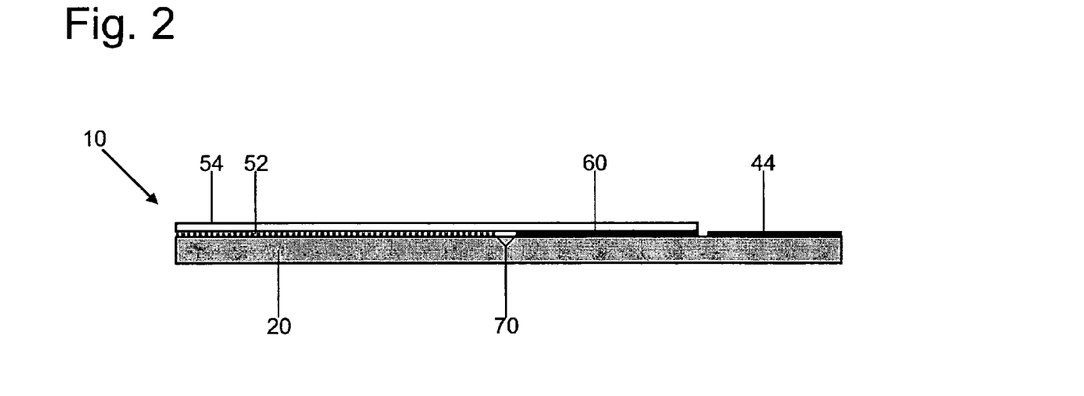
FIG. 2 is a side view of the measuring device of FIG. 1 taken along the line A-A.

In FIG. 2, it is seen that carrier 20 with its means for the deriving electrical signals is protected from external influences. For this purpose, there is attached to its longitudinal edges 24 an elongated support 52 in the form of two strips lying opposite one another. Each of them consists of a layer either of melt adhesive or of a polymeric material. They extend only over part of the two longitudinal edges of carrier 24 up to interstice 70. In one variant (not shown), however, they can extend along the entire length of carrier 24 and even in some cases extend along the short sides of carrier 20. On the one hand, this makes sample application zone 22 smaller and, on the other hand, it supports and protects contacts 44. If, in a development of this variant, good aeration of measuring device 10 is desired, support 52 is interrupted in the region of interstice 70.

Cover 54 is permanently adhesively attached to elongated support 52 such that reaction and detection chamber 50 is formed upstream of interstice 70 acting as an air gap. Cover 54 is designed in the embodiment of FIG. 2 such that it projects beyond interstice 70 and rests against liquid absorption element 60. In two variants (not shown), however, only reaction and detection chamber 50 or else reaction and detection chamber 50 together with interstice 70 are covered. Finally, cover 54, which acts as a hood, can also lie exclusively on elongated support 52 or even be integral therewith.

Usually, preferably single-piece cover 54 consists of one of the polymeric materials mentioned below, which for constructive reasons, if possible, is identical with that of carrier 20. It possesses at least one slot-shaped or semicircular opening 56 by means of which at least one measuring sample or at least one reaction-specific substrate can be applied to carrier 20. Any desired shape of opening(s) 56 can be chosen, depending on the amount and composition of the solutions to be applied.

Reaction and detection chamber 50 is situated between sample application zone 22 and interstice 70. As a rigid structure, it has defined dimensions and has a constant capacity for liquid. Because it is open in the downstream and upstream directions, the measuring sample can flow through it. In its downstream part there are disposed reference electrode 30 and at least one working electrode 40, and optionally parts of conducting tracks 42. If large measuring sample volumes are to be measured, reaction and detection chamber 50 is made larger. This is achieved by making the strips of elongated support 52 thicker.

The measuring sample or the solution containing the reaction-specific substrate penetrates rapidly and uniformly into reaction and detection chamber 50 if its inner surfaces formed by carrier 20, elongated support 52 and cover 54 are treated with surface-active substances such as, for example, detergents. In an advantageous development of this feature, hydrophobic surface-active substances are situated on the inner surfaces in the region of sample application zone 22. The amount of said substances decreases continuously in favor of a hydrophilic detergent layer, the more so the longer the downstream distance is. In the region of electrodes 30, 40, finally, only hydrophilic detergents are present on the inside surfaces. Such an arrangement of surface-active substances in reaction and detection chamber 50 causes the aqueous samples to rapidly reach the vicinity of electrodes 30, 40 located downstream.

Interstice 70 borders upstream on reaction and detection chamber 50 and downstream on liquid absorption element 60. As can be seen from FIG. 1, it is situated on carrier 20 downstream of electrodes 30, 40. This is an important feature of the invention, since it represents a contributing or decisive factor in ensuring that always only an exactly defined measuring sample volume is present in reaction and detection chamber 50. As an air gap, said interstice moreover influences the flow behavior of a measuring sample on carrier 20. Interstice 70 is variable in length and is adjusted to suit the amount of liquid sample used. Larger amounts of sample necessitate a greater distance between reaction and detection chamber 50 and liquid absorption element 60 and thus a larger interstice 70, whilst smaller amounts of measuring sample necessitate a smaller interstice.

In a development (not shown), interstice 70 is delimited laterally by elongated support 52. Slots incorporated therein, preferably between reaction and detection chamber 50 and liquid absorption element 60 guarantee finely regulated aeration and thus change the flow behavior of the measuring sample.

If its flow characteristics are to be additionally influenced, the carrier surface can be coated in the region of interstice 70 with selected surface-active substances. For this purpose, hydrophobic compounds are preferably chosen, such that the region of reaction and detection chamber 50 containing hydrophilic substances is framed upstream by the hydrophobic sample application zone 22 and downstream by the hydrophobic interstice 70.

Liquid absorption element 60 follows the interstice 70 in downstream direction and consists of a bibulous and porous material. It absorbs the liquid measuring sample which has already passed through reaction and detection chamber 50 and interstice 70. As shown in FIG. 2, it forms a finishing edge flush with cover 54 at its downstream end such that the contacts 44 disposed downstream thereof are exposed.

For absorption element 60, all materials are suitable which are able to absorb liquid rapidly. Examples thereof are fibrillar nonwovens or fabrics such as paper, paper pulp, glass fibers, cellulose materials or porous plastics such as polypropylene, polyethylene, polyvinylidene fluoride, ethylenevinyl acetate, acrylonitrile and polytetrafluoroethylene. The fibers run, in a further embodiment of liquid absorption element 60 parallel to the direction of flow of the measuring sample in order to achieve an exclusively unidirectional action, i.e. a sucking action directed downstream, of fibrillar material such as paper.

Particularly good liquid absorption is achieved by the use of a liquid absorption element 60 that has been pretreated with surface-active substances. To this end, it is wetted or impregnated e.g. with dissolved detergents before mounting it onto carrier 20. Such detergents are hydrophilic compounds if the measuring solution is hydrophilic and hydrophobic substances in the case of a correspondingly hydrophobic measuring sample.

The surface-active substances used for the various components of measuring device 10 consist of at least one hydrophilic group and at least one hydrophobic moiety. The latter part comprises alkyl chains having from 10 to 18 carbon atoms. The hydrophilic character of the surface-active substances results because the alkyl structures mentioned are provided with at least one of the polar groups —COOMe, —OSO$_3$Me, —SO$_3$Me, —NH$_2$, =NH, —N$^+$(R)$_3$. Particularly good wetting results are achieved if the surface-active substance, also called a detergent, possesses the empirical formula $C_{20}H_{37}NaO_7S$ or alternatively the formula $C_{18}H_{29}NO_3S$.

Polymeric materials are used for carrier 20, elongated support 52 and cover 54, i.e. for all those parts which form a housing-like portion of measuring device 10. These support device 10 and stiffen it to a certain degree. The polymers involved are those selected from the group consisting of the polyethylenes, polystyrenes, polyurethanes, polyvinyl acetates, and polyesters, for example polyethylene terephthalates. Polymers selected from the group consisting of epoxy resins, methacrylic polymers, polycarbonates, and chlorinated polyvinyl compounds (for example polyvinyl chloride) are also used. Copolymers of two or more of the compounds mentioned are also used. Moreover, nitrocellulose and/or cellulose layers, for example, are used on carrier 20 or as the carrier material itself, in order, for example, to create a number of regions having different flow properties in measuring device 10.

A further embodiment of measuring device 10 of the invention consists of a carrier 20 in the form of a foil, onto which three electrodes 30, 40, 40 are printed. Reference electrode 30, usually arranged in the center of the carrier, is surrounded by two working electrodes 40, 40. Each of these working electrodes 40, 40 is provided with a variety of ligands and/or biologically active specific binding molecules, which can in turn be bound to catalytically active proteins. This measuring device 10 can be built in two differenr designs, namely one (not shown) having two specific working electrodes 40', 40' and one, illustrated in FIG. 3, which has a specific and a nonspecific working electrode 40', 40".

Figure 3:
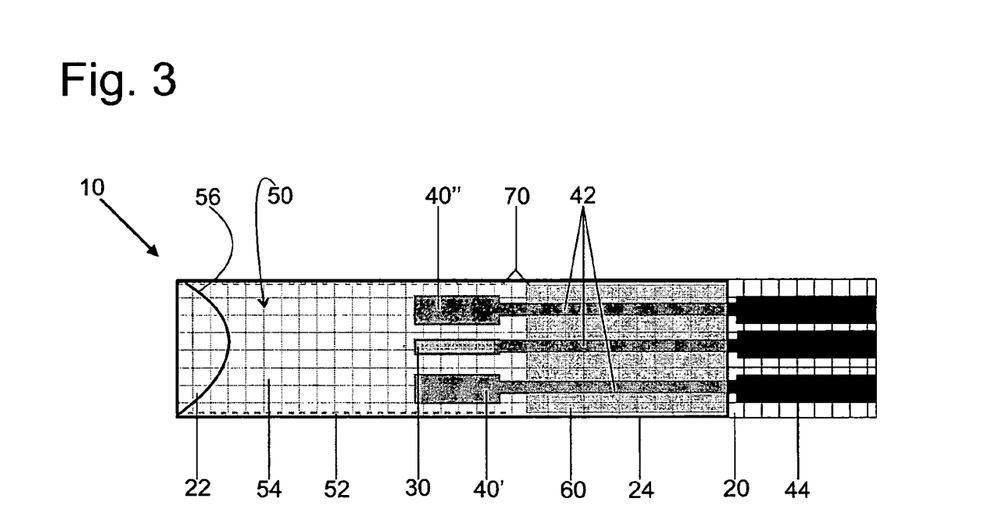
FIG. 3 is a top view of a measuring device having two working electrodes.

In the first design, each working electrode 40', 40' possesses ligands and/or biologically active specific binding molecules, which in each case can selectively bind and detect an analyte in the measuring sample. Accordingly, this allows two different analytes within a single sample to be jointly detected independently of one another.

Nonspecific working electrode 40" of the second design is provided with nonspecific biologically active binding molecules, preferably of proteinogenic nature, for example with species of immunoglobulins. It binds a variety of constituents of the measuring sample, which can lead to corrupted signals at the specific working electrode 40'. Such an arrangement is suitable for detecting or filtering out a signal produced by nonspecific binding of electroactive constituents and thus increases the sensitivity of the test.

Figure 4:
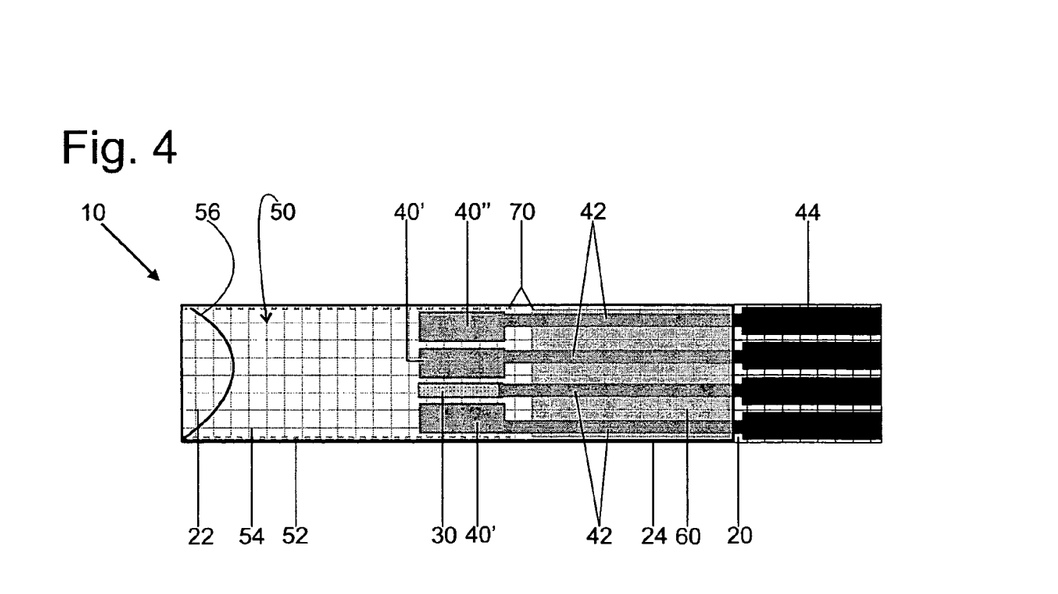
FIG. 4 is a top view of a measuring device having three working electrodes.

A further form of measuring device 10 according to the invention processes three working electrodes 40, 40, 40. These can be specific and/or nonspecific to an analyte. As a rule, according to FIG. 4 a nonspecific working electrode 40"

and two specific working electrodes 40', 40' are provided. They can have any desired arrangement on the carrier 20, but care should be taken to ensure that reference electrode 30 is in a central position.

For the production of measuring device 10 according to the invention, a carrier 20 which consists of one of the polymeric materials mentioned is used as a basis. For certain applications, this is coated in order to inactivate active groups which are possibly present or to prepare its surface for the binding of further molecules. To this end, it is usual to apply a primer solution containing the constituents necessary for the coating onto the carrier 20, which is subsequently dried.

After this, the means for deriving electrical signals are applied, that is to say, electrodes 30, 40, conducting tracks 42 and contacts 44. This is done by placing an arrangement consisting of these constituents on the carrier surface or printing the latter by a screen printing process using the aforementioned electrically conducting pastes. These transfer a chemoelectric signal particularly well if they are admixed with a mediator such as ferrocenedicarboxylic acid. In addition they can already be provided with ligands, biologically active specific or nonspecific binding molecules and/or catalytically active proteins. Such a procedure, however, is only possible if the particle-selective compounds mentioned are stable during subsequent drying of the pastes at elevated temperature.

If none or only some of the ligands, biologically active binding molecules or catalytically active proteins should be stable during the drying process, they must be applied subsequently as a layer to working electrode(s) 40. In order to bond them covalently to an electrode surface, various coupling reagents are used. Examples of these are glutaraldehyde, acid chlorides, anhydrides, active esters, azides, diazo compounds, succinimides, and carbodiimides (Wong, S. S., Chemistry of Protein Conjugation and Cross-Linking. Florida: CRC Press, 1991). The substances can be homobifunctional or hetero-bifunctional compounds (cross-linkers). "Bifunctional" means here that the compounds possess two reactive groups connected via a hydrocarbon chain, whilst "homo" signifies that these groups are identical and "hetero" that they are different.

Coupling reagents are also used in order to connect ligands and biologically active binding molecules and/or catalytically active proteins to the coated or uncoated carrier surface. Moreover, they are needed in order to link the said molecules chemically in all conceivable combinations with one another.

In a development of the invention, at least one working electrode 40 carries no particle-selective compounds. The ligands and/or biologically active binding molecules and/or catalytically active proteins are, instead, permanently immobilized on the carrier 20 in the immediate vicinity of electrodes 30, 40 using the coupling reagents indicated.

After particle-selective compounds have been applied undetachably to carrier 20 and/or electrodes 30, 40, other ligands and/or biologically active specific binding molecules, which can be linked to catalytically active proteins, are dried in, or immediately downstream of, sample application zone 22 in such a way that they are mobile in the moist state. In order to keep them in the native form or to remobilize them easily, they are usually applied in a solution which contains auxiliaries such as polyhydroxy compounds and/or polyhydroxycarbonyl compounds or globular proteins.

Liquid absorption element 60 is now impregnated with a solution of one of the surface-active substances mentioned, dried, and fixed with an adhesive means to carrier 20. According to the embodiments illustrated in FIGS. 1 to 4, it is to be attached such that the major part of conducting tracks 42 is covered, whilst electrodes 30, 40 and contacts 44 remain exposed. Normally, liquid absorption element 60 directly engages the carrier surface 20 provided with conducting tracks 42 but, it can also be fixed to carrier 20 by its longitudinal sides only, so that a hollow space remains between it and carrier 20.

Next, elongated support 52 is fixed to longitudinal edges 24 of carrier 20, and cover 54 is then attached. The latter is firmly connected to elongated support 52 and, in a modification, also to liquid absorption element 60. It is assembled such that sample application zone 22 is located below one of its openings 56. Thus a measuring device 10 having a reaction and detection chamber 50, interstice 70, and liquid absorption element 60 is obtained.

In a preferred development, elongated support 52 and cover 54 are treated before assembly with a solution of the surface-active substances and dried. In a particularly efficient variant of this embodiment, regions of cover 54, support 52 and, optionally, carrier 20 forming said reaction and detection chamber 50 are coated with hydrophilic substances and the regions disposed downstream and upstream of reaction and detection chamber 50 are coated with hydrophobic compounds.

In a development (not shown) of measuring device 10 according to the invention, the two opposing strips of elongated support 52 are each attached to carrier 20 as two parts, that is to say, in all, four strips are attached to carrier 20. A first strip extends from the upstream end of carrier 20 as far as interstice 70 and a second strip from interstice 70 as far as contacts 44. Strips three and four run parallel to the first two strips on the opposite longitudinal edge 24 of carrier 20. Using such a design, cover 54 can be fixed entirely to elongated support 52 and can cover liquid absorption element 60 such that a gap remains between it and cover 54. This is convenient in order to offer adequate space for liquid absorption element 60 when this is impregnated, and therefore swollen, with the measuring sample and substrate solution.

In order to determine the amount of analyte in a sample liquid, measuring device 10 is connected to an electrical measuring apparatus and a measuring sample is applied. If it contains the analyte, this will bind, either in sample application zone 22 or immediately downstream thereof, to mobile biologically active specific binding molecules present therein. Each of these carries a catalytically active protein and forms a complex with the analyte.

This complex migrates with the sample solution due to capillary action and, on account of the measuring device 10 being coated with detergents, automatically enters the dimensionally stable reaction and detection chamber 50. There it binds to immobilized ligands or to immobilized biologically active specific binding molecules, which are arranged either on at least one working electrode 40 or in its immediate vicinity. The sandwich arrangement thus formed consists of the mobile particle-selective compound, the analyte, and the immobile particle-selective compound.

Excess sample solution flows downstream into interstice 70 and thence into liquid absorption element 60. However, this does not take place continuously, because an equilibrium is established between the sucking action of liquid element 60, on the one hand, and the retention action in the reaction and detection chamber 50, on the other hand. When the measuring solution flowing downstream is no longer present on sample application zone 22, the sucking action continues until an interruption of the flow of measuring solution occurs in the region of interstice 70, which is designed as an air gap. Thus some of the sample solution is taken up by liquid absorption element 60, while a further defined volumetric portion remains in reaction and detection chamber 50. This portion, which is always constant, depends on the size of interstice 70. If its dimensions are deliberately specified when designing the measuring device 10, there is the assurance that a constant measuring volume will always be present in reaction and detection chamber 50. This design measure considerably increases the accuracy of a quantitative analyte determination and is an important feature of the invention. This also applies if interstice 70 is designed to be very small, that is to say, is macroscopically not present.

After the constant volumetric portion of the measuring solution has been left in reaction and detection part 50 for from 5 to 600 seconds, but ideally for from 20 to 60 seconds, and it has accordingly been possible for the analyte to form a sandwich in the manner described, a liquid is applied in a second step, to sample application zone 22, which liquid contains a reaction-specific substrate for at least one catalytically active protein. This is usually a buffered solution whose volume is at least three times as large as the volume of the measuring sample. By this means, any measuring solution still present in reaction and detection chamber 50 is rinsed out, flows into interstice 70 and is absorbed by liquid absorption element 60. Simultaneously, the reaction-specific substrate reacts with the amount of catalytically active protein which has been retained in the sandwich compound in reaction and detection chamber 50. An electroactive substrate form is formed, which is oxidized or reduced, in any case electrochemically reacted, on the, or a, working electrode 40. In this process, a current/voltage change occurs, which can be read off on a potentiostat. The size of the change in the electrical signal is a measure of the amount of reacted reaction-specific substrate and thus of the amount of bound catalytically active protein. Consequently, it is a measure of the amount of sandwich compound on, or in the vicinity, of working electrode(s) 40 and thus indicates the amount of analyte in the measuring solution.

In one form of the measuring device 10, a first catalytically active protein converts a reaction-specific substrate to a reaction-specific substrate 2. This it is that reacts with a second catalytically active protein to produce an electroactive substrate form which, as described above, is caused to react on at least one working electrode 40. The second catalytically active protein is usually immobilized on working electrode 40 or in its immediate vicinity. In a modification of the invention, it is added, however, to the buffered solution of the reaction-specific substrate.

If the amount of an analyte is determined using the measuring device 10 represented in FIG. 3, and if a specific and a nonspecific working electrode 40', 40" are used, two electrical signals are obtained. The signal from nonspecific working electrode 40" must then be subtracted from that of specific electrode 40' in order to obtain relevant values for the respective analyte.

The invention is illustrated with reference to the following exemplary embodiments which, however, only illustrate a section of all combinations which can be covered by the present invention.

EXAMPLE 1a

Production of a Two-Electrode Measuring Device 10 According to FIG. 1

The starting material for working electrode 40 of device 10 is an aqueous graphite composition (Deltaforge GP-157, Acheson, US) which contains 3.56 mg of ferrocenedicarboxylic acid per 1 g of graphite composition. To this mixture is added a 0.01 molar phosphate-buffered solution of pH 7.5, in which 25% (w/v) of phenylboronic acid and 9 g/l of NaCl are dissolved, and the whole is mixed to give a graphite paste. For all conductive tracks 42 and contacts 44, a graphite paste is used which contains no additives (C2000802D2, Gwent Electronic Materials Ltd., UK). Reference electrode 30 is produced using a conventional silver/silver chloride paste (C61003D7, Gwent Electronic Materials Ltd., UK). As a material for an insulating layer, a dielectric polymer (D2000222D2, Gwent Electronic Materials Ltd., UK) is used.

First, conductive tracks 42 and contacts 44 are printed onto a PVC film (10×50 mm) by means of a screen printing technique as shown in FIG. 1, and this is dried for 5 min at 100° C. Subsequently, using the same technique the insulating layer of dielectric polymer is applied for delimitation of the electrode surfaces and dried at 80° C. for 30 minutes. Then, in the same manner, the pastes for working electrode 40 and reference electrode 30 are applied in succession and the former is dried for 5 min at 100° C. and the latter for 10 min at 80° C.

Upstream, 5 μl of a 0.3 molar mannitol solution, which contains anti-hemoglobin A1c (monoclonal)-glucose dehydrogenase conjugate (anti-HbA1c-GDH conjugate) in a concentration of 1 mg/ml, are then applied to carrier 20. Moreover, the solution contains 0.3 mmol/l of a protein obtained from horse serum, which is precipitated by an 80% ammonium sulfate solution and is soluble in pure water. Carrier 20 coated in this way is dried at 40° C. in vacuo.

As liquid absorption element 60, a fiber nonwoven (Schleicher & Schüll 0966, 8×25 mm) is used. It is impregnated with a solution of 3 g of $C_{20}H_{37}NaO_7S$ in 100 ml of purified water, dried in a warm stream of air and fixed to carrier 20. It is applied downstream of the electrodes 30, 40 such that it does not directly abut them, but a small gap or interstice 70 remains free.

Elongated support 52 is attached to longitudinal edges 24 of carrier 20, and cover 54 measuring 10×22 mm and consisting of polyester is fixed thereto. This is, as can be seen from FIG. 1, attached such that its semicircular opening 56 leaves sample application zone 22 exposed.

EXAMPLE 1b

Determination of Hemoglobin A1 c (HbA1c)

A substrate solution is prepared which consists of 6.5 ml of a phosphate-buffered saline solution (PBS solution), 3.25 ml of a phosphate-buffered saline-glucose solution (PBS glucose solution), and 0.25 ml of a solution of β-nicotinamide adenine dinucleotide (NAD). The PBS solution contains 0.12 mol/l of phosphate, 0.15 mol/l of NaCl and has a pH of 7.6. The PBS-glucose solution additionally comprises glucose in a concentration of 0.1 g/ml. Die NAD solution has a concentration of 80 mg/ml.

Measuring device 10 described in Example 1a is connected to a potentiostat and 10 μl of HbA1c control blood (Biocon) are added to sample application zone 22. After an incubation time of 20 seconds, 30 μl of substrate solution are applied by pipette and the mixture is incubated for a further 20 seconds. A resultant current or voltage change is then read off on the potentiostat.

EXAMPLE 1c

Determination of Hemoglobin A1c (HbA1c) in a Control Experiment

In a parallel experiment, a further sample of the control blood used (Biocon) is subjected to an HbA1c microcolumn test (Biocon 11044).

EXAMPLE 1d

Determination of the Total Amount of Hemoglobin Using a Pt Electrode

In a further parallel experiment, a platinum electrode is immersed in a known manner in a sample of the above control blood solution, in which a hexacyanoferrate II salt (ferrocyanide) has been previously dissolved. This is oxidized by the hemoglobin present to form hexacyanoferrate III (ferricyanide) and reduced electrochemically on the platinum electrode back to ferrocyanide. The electrical signal thus generated indicates the total amount of hemoglobin in the control blood sample.

EXAMPLE 1e

Determination of the Proportion of Hemoglobin A1c (HbA1c) in the Total Amount of Hemoglobin For the determination of the proportion of hemoglobin A1c (HbA1c) in all hemoglobin present, the total amount of hemoglobin determined in Example 1d is related to the readings obtained in Examples 1b and 1c. The following percentage proportions are the result:

| | |
|---|---|
| Proportion of HbA1c determined using measuring device 10 according to the invention | 4.90% |
| Proportion of HbA1c determined on a microcolumn (Biocon 11044) | 4.40% |

EXAMPLE 2a

Production of Another Two-Electrode Measuring Device 10 According to FIG. 1

The starting material for the working electrode 40 of this device 10 is an aqueous graphite composition (Deltaforge GP-157, Acheson, US) which contains 3.56 mg of ferrocenedicarboxylic acid per 1 g of graphite composition. 250 µl of a commercially available solution of Gelafusal® (nitrogen content 0.9 g/100 ml) are added to this mixture and the whole is mixed to give a graphite paste. For all conductive tracks 42 and contacts 44, a graphite paste is used which contains no additives (C2000802D2, Gwent Electronic Materials Ltd., UK). The reference electrode 30 is produced using a conventional silver/silver chloride paste (C61003D7, Gwent Electronic Materials Ltd., UK). As a material for an insulating layer, a dielectric polymer (D2000222D2, Gwent Electronic Materials Ltd., UK) is used.

First, conductive tracks 42 and contacts 44 are printed onto a PVC film (10×50 mm) by means of a screen printing technique, as shown in FIG. 1, and this is dried for 5 min at 100° C. Subsequently, using the same technique, the insulating layer of dielectric polymer is applied for delimitation of the electrode surfaces and dried at 80° C. for 30 minutes. Then, in the same manner, the pastes for working electrode 40 and reference electrode 30 are applied in succession and the former is dried for 5 min at 100° C. and the latter for 10 min at 80° C.

A biologically active specific binding molecule and a catalytically active protein are then applied to working electrode 40. Both compounds can be present in immobilized form, both bound to one another and also bound individually to working electrode 40.

First, a 0.1 molar 2-(N-morpholinoethanesulfonic acid) buffer solution (MES buffer solution) is prepared which contains 0.15 mol/l of NaCl and possesses a pH of 4.7. Then, a 10 percent (w/v) aqueous solution of (ethyldimethylaminopropyl)carbodiimide (EDC solution) and a 14 percent (w/v) solution of sodium N-hydroxysuccinimide-sulfonate are freshly prepared. Moreover, a coupling buffer having a pH of 7.5 is prepared. It contains 0.1 mol/l of sodium dihydrogenphosphate, 0.1 mol/l of disodium hydrogenphosphate and 0.15 mol/l of sodium chloride. Finally, a protein/hexitol solution is prepared which contains 5 g/l of albumin from bovine serum and 0.50 mol/l of sorbitol.

5 mg of an anti-streptococci-A antibody and 5 mg of glucose oxidase are dissolved in 1 ml of the MES buffer solution. 1 ml of EDC solution and 1 ml of the succinimide solution are added to this solution and it is made up to 5 ml with MES buffer solution. The solution obtained can be incubated for 15 minutes on a rotating device, which causes anti-streptococci-A and glucose oxidase to change into a chemically reactive form.

5 µl of this solution and 5 µl of coupling buffer are pipetted onto working electrode 40 and allowed to act for 30 minutes. These are then aspirated, 5 µl of the protein/hexitol solution is applied to working electrode 40, and carrier 20 is dried together with electrodes 30, 40 in vacuo for 1 h at 30° C. to 50° C.

Upstream, 5 µl of a 0.3 molar alpha-D-glucopyranosyl-beta-D-fructofuranoside solution which contains rabbit anti-streptococci-A-peroxidase conjugate (anti-Strep-A-POD-conjugate) in a concentration of 1 mg/ml are then added to carrier 20. Moreover, this solution contains 0.3 mmol/l of a protein obtained from equine serum, which is precipitated using an 80 percent ammonium sulfate solution and is soluble in pure water. The carrier 20 coated in this way is dried in vacuo at 40° C.

As liquid absorption element 60, a fiber nonwoven (Schleicher & Schüll 0966, 10×25 mm) is used. It is impregnated with a solution of 3 g of $C_{20}H_{37}NaO_7S$ in 100 ml of purified water, dried in a warm stream of air and fixed to carrier 20. It is applied downstream of the electrodes 30, 40 such that it does not directly abut them, but a small gap or interstice 70 remains free.

Elongated support 52 is attached to the longitudinal edges 24 of carrier 20, and cover 54 measuring 10×22 mm and consisting of polyester is fixed thereto. This is, as can be seen from FIG. 1, attached such that its semicircular opening 56 leaves sample application zone 22 exposed.

EXAMPLE 2b

Determination of Streptococci A Antigen

A nitrite solution is prepared which contains 1 mol/l of sodium nitrite. A 0.1 molar glycine solution is then prepared, which is brought to a pH of 2.5 with hydrochloric acid. Moreover, a 0.2 molar tris buffer solution having a pH of 9 and an aqueous substrate solution which contains 20 mmol/l of β-D-glucose and 3 mmol/l of potassium iodide is prepared.

Two throat swabs each are taken from two patients:

Patient 1: age 7 years, sex: male, reason for visit to doctor: cold symptoms, airways infection;

Patient 2: age 5 years, sex: female; reason for visit to doctor: sore throat.

200 µl of the glycine solution are mixed with 200 µl of the nitrite solution in an extracting vessel. The first swab from a patient is immersed in this and extracted for two minutes. 200 µl of tris buffer solution are then added. 10 µl of this extraction solution are pipetted onto the sample application zone 22 of measuring device 10, which is connected to a potentiostat, and incubated for 20 seconds. 30 µl of the substrate solution are then applied and again incubated for 20 seconds. The current measured using the potentiostat indicates that no streptococci-A antigen is present in the swab from patient 1, but streptococci-A antigen is present in the swab from patient 2. In this case, the electrical signal obtained corresponds to approximately $4\times10^5$ CFU/ml (=colony-forming units/ml).

EXAMPLE 2c

Determination of Streptococci A Antigen in a Control Experiment

Swab 2 from both patients is transferred to tubes containing transport medium for the purpose of cultural growth of streptococci-A strains. The strains are cultured anaerobically on Schaedler blood agar for 24 hours at 37° C. The qualitative evaluation shows, in agreement with Example 2b, that no streptococci-A antigen is present in the swab from Patient 1, but the swab from Patient 2 contains streptococci-A antigen. The result is based on the confirmation of beta-hemolyzing streptococci of serological group A using a streptococci identification test for the detection of these bacteria (Oxoid). The counting of the streptococci colonies is carried out according to S. Isaac, D. Jennings: Kultur von Mikroorganismen [Culture of Microorganisms], Spektrum Akademischer Verlag Heidelberg, Berlin, Oxford, p. 87 and shows $2\times10^5$ colony-forming units per ml (CFU/ml).

EXAMPLE 3a

Production of a Three-Electrode Measuring Device 10 According to FIG. 3

The starting material for working electrodes 40 of this device 10 is an aqueous graphite composition (Deltaforge GP-157, Acheson, US) which contains 3.56 mg of ferrocene-dicarboxylic acid per 1 g of graphite composition. To this mixture there are added 125 µl of a 20 percent (w/v) solution of polyaminopentanedioic acid in water and the whole is mixed to give a graphite paste. For all conductive tracks 42 and contacts 44, a graphite paste is used which contains no additives (C2000802D2, Gwent Electronic Materials Ltd., UK). Reference electrode 30 is produced using a conventional silver/silver chloride paste (C61003D7, Gwent Electronic Materials Ltd., UK). As a material for an insulating layer, a dielectric polymer (D2000222D2, Gwent Electronic Materials Ltd., UK) is used.

First, conductive tracks 42 and contacts 44 are printed onto a PVC film (10×50 mm) by means of a screen printing technique, as shown in FIG. 3, and this is dried for 5 min at 100° C. Subsequently, using the same technique, the insulating layer of dielectric polymer is applied for delimitation of the electrode surfaces and dried at 80° C. for 30 minutes. Then, in the same manner, the pastes for working electrode 40 and reference electrode 30 are applied in succession and the former is dried for 5 min at 100° C. and the latter for 10 min at 80° C.

A 0.1 molar 2-(N-morpholinoethanesulfonic acid) buffer solution (MES buffer solution) is prepared which contains 0.15 mol/l of NaCl and possesses a pH of 4.7. Then, a 10 percent (w/v) aqueous solution of (ethyldimethylaminopropyl)carbodiimide (EDC solution) and a 14 percent (w/v) solution of sodium N-hydroxysuccinimide-sulfonate are freshly prepared. Moreover, a coupling buffer having a pH of 7.5 is prepared. It contains 0.1 mol/l of sodium dihydrogenphosphate, 0.1 mol/l of disodium hydrogenphosphate and 0.15 mol/l of sodium chloride.

Monoclonal mouse anti-*Chlamydia trachomatis* antibody and glucose oxidase are dissolved in sufficient coupling buffer to produce an antibody concentration of 2 mg/ml and a glucose oxidase activity of 150 U/ml (coupling solution). Moreover, a solution of 2 mg/ml of nonspecific mouse immunoglobulin G and glucose oxidase having an activity of 150 U/ml is prepared in coupling buffer (mouse IgG solution). Finally, a protein/hexitol solution is prepared which contains 5 g/l of albumin from bovine serum and 0.50 mol/l of sorbitol.

4 ml of the MES buffer solution are mixed with 1 ml of the EDC solution and 1 ml of the sodium hydroxysuccinimidesulfonate solution. 5 µl of the mixture of solutions thus obtained are pipetted onto the specific and the nonspecific working electrode 40 and incubated for 15 minutes in order to activate their surfaces.

5 µl of the coupling solution which contains monoclonal mouse anti-*Chlamydia trachomatis* antibody and glucose oxidase are added to activated specific working electrode 40'. 5 µl of the IgG solution are applied to activated nonspecific working electrode 40". After an incubation time of 30 minutes, the solution is aspirated, 5 µl of protein/hexitol solution are pipetted onto working electrodes 40', 40", which are then dried for one hour at 30° C. to 50° C. in vacuo.

Upstream, 5 µl of a 0.5 molar sorbitol solution which contains anti-*Chlamydia trachomatis*-peroxidase conjugate in a concentration of 1 mg/ml are then applied to carrier 20. In addition, this solution contains albumin from bovine serum in a concentration of 5 g/l. Carrier 20 coated in this way is then dried at 40° C. in vacuo.

As liquid absorption element 60, a fiber nonwoven (Schleicher & Schüll 0966, 10×25 mm) is used. It is impregnated with a solution of 3 g of $C_{20}H_{37}NaO_7S$ in 100 ml of purified water, dried in a warm stream of air and fixed to carrier 20. It is attached downstream of the electrodes 30, 40 such that it does not directly abut them but leaves a small gap or interstice 70.

Elongated support 52 is attached to longitudinal edges 24 of carrier 20, and cover 54 measuring 10×22 mm and consisting of polyester is fixed thereto. This, as can be seen from FIG. 3, is attached such that its semicircular opening 56 leaves sample application zone 22 exposed.

EXAMPLE 3b

Determination of *Chlamydia Trachomatis* Antigen

BGM cells from the monkey renal fibroblast cell line ($10^6$ cells) are raised in culture bottles (25 cm$^2$) in an Eagle medium containing 10 percent fetal calf serum to give a dense cell lawn. After aspirating the medium, it is inoculated with 1 ml of *Chlamydia trachomatis* suspension. The *Chlamydia trachomatis* pathogen is an L2 strain, which was obtained from the Institute for Medicinal Microbiology of the Friedrich-Schiller University Jena and was adjusted to a content of $1\times10^6$ IFU/ml(=infectious units/ml). For complete infection, the suspension is kept for 2 hours at 37° C., and it is then incubated for 3 days at the same temperature under a 5 percent $CO_2$ atmosphere. The cells obtained are disrupted by ultrasonic treatment and serve as a positive control.

An aqueous substrate solution is prepared which contains 20 mmol/l of β-D-glucose and 3 mmol/l of potassium iodide.

10 µl of the *Chlamydia trachomatis* positive control are pipetted onto sample application zone 22 of measuring device 10, which is connected to a potentiostat, and incubated for 20 seconds. 30 µl of the substrate solution are then applied and again incubated for 20 seconds. The potentiostat indicates an electrical signal which, according to the calibration curve, corresponds to a *Chlamydia trachomatis* antigen titer of 1:256. Titer is understood as meaning the final dilution of a geometrical dilution series in which a positive reaction is just still indicated.

EXAMPLE 3c

Determination of the Content of *Chlamydia Trachomatis* Antigen in a Control Experiment Using a Chlamydia antigen ELISA, Chlamidia "Celisa", Cellabs Diagnostics PTY, Australia, a titer of 1:256 is determined.

The invention is not restricted to the previously described embodiments, but can be modified in a variety of ways.

Thus, carrier 20 and cover 54 can also be formed from inorganic materials such as glass, ceramics or graphite.

Moreover, measuring device 10 can also be designed according to the principle of a competitive binding assay. For this purpose, no mobile, biologically active specific binding molecules, which are mobile in the moist state, are applied to carrier 20, but it is coated with a conjugate of analyte and catalytically active protein, which conjugate is mobile in the moist state. As long as the sought-after analyte is not present in the measuring sample, the conjugate flows downstream and binds completely to the biologically active specific binding molecules immobilized on at least one working electrode 40 or in its vicinity. If, however, analyte is present in the measuring sample, it competes with the conjugate for binding sites of the immobilized biologically active specific binding molecules. Accordingly, an unbound part of the conjugate flows further into interstice 70 and thence into liquid absorption element 60. Since less conjugate is fixed in the region of working electrode 40, less substrate can be reacted, which leads to a smaller electronic signal at working electrode 40. The decrease in the signal level is a quantitative measure of the amount of analyte in the measuring sample.

It is apparent that a measuring device 10 for the detection and the determination of the concentration of at least one analyte in a liquid medium consists of a polymeric carrier 20 having biologically active specific binding molecules dried on its upnstream portion. A multiple electrode set consisting of at least one reference electrode 30 and at least one working electrode 40 is located thereon in a downstream region. Said working electrode 40 is provided with biologically active specific binding molecules. Carrier 20 has a sample application zone 22, downstream of which a through-flow non-deformable reaction and detection chamber 50, an interstice 70, variably dimensioned, and a liquid absorption element 60 are attached. For a qualitative and quantitative analyte determination, two liquid media are applied in succession to sample application zone 22, namely a sample solution and a substrate solution. While the first can contain the wanted analyte, the second provides for the formation of an electrical signal. As a result of the design of reaction and detection chamber 50 and interstice 70, which are geometrically regular and not deformable by fluid media, exact measurements can be carried out.

All features and advantages arising from the claims, the description, and the drawings, including constructive details, spatial arrangements and process steps, can be essential to the invention both per se and in a great variety of combinations.

LIST OF REFERENCE SYMBOLS 10 measuring device
20 carrier
22 sample application zone
24 longitudinal edge
30 reference electrode
40, 40', 40" working electrode
42 conductive track
44 contact
50 reaction and detection chamber
52 elongated support
54 cover
56 recess/opening
60 liquid absorption element
70 interstice

The invention claimed is:

1. A device for the detection and/or determination of the concentration of at least one analyte present in a liquid medium, consisting of
   a) a strip-shaped carrier (20) having two longitudinal edges (24), to which carrier (20) a printed multiple electrode set consisting of at least one reference electrode (30) and at least one working electrode (40) is applied and
   b) ligands which are suitable for binding a biologically active specific binding molecule or the analyte,
   wherein the device
   comprises a rigid reaction and detection chamber (50) adapted for continuous flow of the medium along said strip-shaped carrier (20), said reaction and detection chamber being formed by an elongated support (52) applied to said longitudinal edges (24) of said carrier (20) having a cover (54) disposed on said support (52), and that
   a liquid absorption element (60) is disposed downstream of said reaction and detection chamber (50), and
   further wherein the elongated support (52) is divided in two and is permanently adhesively attached, in the form of two strips, to the two longitudinal edges (24) of said carrier (20) and said strips only lie on one part of said two longitudinal edges (24) of said carrier (20), there being an interstice (70) between said strips and said liquid absorption element (60) from which interstice (70) said strips extend upstream on said longitudinal edges (24).

2. The device as claimed in claim 1, wherein said carrier (20) is designed as a self-supporting flow surface for the liquid medium.

3. The device as claimed in claim 1, wherein said carrier (20) is unitary and consists of a polymeric, nonconducting, preferably rectangular shape.

4. The device as claimed in claim 1, wherein said ligands and/or biologically active specific binding molecules are applied to said carrier (20).

5. The device as claimed in claim 4, wherein said ligands and/or said biologically active specific binding molecules are immobilized on said carrier (20).

6. The device as claimed in claim 1, wherein said carrier (20) is provided with a base coating which consists of proteins selected from the group consisting of the animal or human albumins and/or from the group consisting of the globulins and/or from the group consisting of the glycoproteins.

7. The device as claimed in claim 1, wherein said carrier (20) is provided with a base coating which consists of polypeptides, such as polyamino acids and/or degradation products of proteins, preferably of the supportive and connective tissue.

8. The device as claimed in claim 1, wherein a sample application zone (22) is formed on one end of said carder (20).

9. The device as claimed in claim 8, wherein said sample application zone (22), or at least a part thereof, is treated with surface-active substances and possesses the ability to absorb the liquid medium.

10. The device as claimed in claim 8, wherein a mesh-like or porous material, preferably treated with surface-active substances, is provided on said sample application zone (22).

11. The device as claimed in claim 1, wherein each working electrode (40) and each reference electrode (30) is connected conductively to a conductive track (42) assigned thereto, and each conductive track (42) is conductively connected to an assigned contact (44) which is connectable to an electrical measuring apparatus.

12. The device as claimed in claim 11, wherein at least one of said electrodes (30, 40) and its assigned conductive track (42) and its assigned contact (44) consists of gold, silver, platinum, nickel, palladium, titanium, copper, or carbon.

13. The device as claimed in claim 1, wherein at least one of said electrodes (30, 40) consists of a dried graphite paste or is an electrode to be prepared from metal pastes and/or metal salt pastes by drying.

14. The device as claimed in claim 1, wherein at least one of said working electrodes (40) carries ligands and/or biologically active specific binding molecules, on its surface.

15. The device as claimed in claim 1, wherein reaction-nonspecific binding molecules are disposed and/or immobilized on at least one further working electrode (40).

16. The device as claimed in claim 1, wherein said ligands are applied as a solution having a concentration of 0.0007 to 0.7 mol/l, preferably of 0.035 to 0.35 mol/l.

17. The device as claimed in claim 1, wherein said ligands are formed from ribonucleic acids or deoxyribonucleic acids.

18. The device as claimed in claim 1, wherein said ligands consist of aminocarboxylic acids, preferably diaminocarboxylic acids.

19. The device as claimed in claim 18, wherein said ligands consist of non-monomeric homodet or heterodet aminocarboxylic acids of the composition R—CH(NH$_2$)—(CH$_2$)$_n$—COOH linked in peptide-like form, for example of polyaminocarboxylic acids, where R stands for a proton or preferably for an amino, imino, hydroxyl, thiol, hydroxyalkyl, aminoalkyl or carboxyalkyl group and n assumes a value of from 0 to 6, preferably 0.

20. The device as claimed in claim 1, wherein said ligands consist of proteides or of proteins which preferably originate from the bacterium *Streptomyces avidinii*.

21. The device as claimed in claim 1, wherein the detection of HbA1c, at least one ligand is a phenylboronic acid.

22. The device as claimed in claim 1, wherein said biologically active specific binding molecules possess binding sites for at least one ligand or are bound thereto.

23. The device as claimed in claim 1, wherein said biologically active specific binding molecules have at least one specific binding region for binding an analyte.

24. The device as claimed in claim 1, wherein a catalytically active protein is preferably covalently bonded to said biologically active specific binding molecules and/or said ligands or a number of catalytically active proteins are preferably covalently bonded to said biologically active specific binding molecules and/or said ligands.

25. The device as claimed in claim 1, wherein said strips consist of a polymer material and/or of a melt adhesive and possess the same thickness as said liquid absorption element (60).

26. The device as claimed in claim 1, wherein said cover (54) consists of a polymeric, preferably rectangular, shape and is connected to said elongated support (52) in such a way that it covers, said carrier (20) and also said multiple electrode set and said liquid absorption element (60).

27. The device as claimed in claim 1, wherein said cover (54) only covers one or more parts of said carrier (20).

28. The device as claimed in claim 8, wherein said cover (54) possesses on its upstream side at least one slot-shaped and/or semicircular or polygonal recess (56) and/or opening (56), which is arranged in such a way that said sample application zone (22) of said carrier (20) can be charged with liquid medium.

29. The device as claimed in claim 1, wherein said liquid absorption element (60) is adhesively fixed to that side of said cover (54) which faces said carrier (20).

30. The device as claimed in claim 1, wherein said cover (54) or at least a part thereof is treated with surface-active substances.

31. The device as claimed in claim 8, wherein the side of said cover (54) facing said carrier (20) in the region of said multiple electrode set, in particular above said working electrode(s) (40) and above said reference electrode (30) possesses hydrophilic properties and has, at least in part, a hydrophobic surface in the region of said sample application zone (22).

32. The device as claimed in claim 1, wherein said reaction and detection chamber (50) is open in the downstream and upstream directions and said interstice (70) borders on its downstream end.

33. The device as claimed in claim 11, wherein said liquid absorption element (60) is disposed on said carrier (20) at a downstream distance from said sample application zone (22) and covers said conductive tracks (42), preferably rests directly thereon.

34. The device as claimed in claim 1, wherein said liquid absorption element (60) consists of an absorbent porous fibrillar material and is fixed adhesively to said carrier (20).

35. The device as claimed in claim 32, wherein said porous material is constructed from at least one fiber layer or at least one fabric, which consists of cellulose fibers or glass fibers or mixtures thereof or is composed of organic polymers.

36. The device as claimed in claim 1, wherein said liquid absorption element (60) is treated with surface-active substances, preferably with those having hydrophilic properties.

37. The device as claimed in claim 9, wherein said surface-active substances contain hydrophilic groups, such as —COOMe, —OSO$_3$Me, —SO$_3$Me, —NH$_2$, or =NH, —NR$_3^+$ and hydrophobic alkyl chains having from 10 to 18 carbons or alkylaryl groups.

38. The device as claimed in claim 9, wherein the surface-active substances used are preferably substances having the empirical formulae C$_{20}$H$_{37}$NaO$_7$S or C$_{18}$H$_{29}$NO$_3$S.

39. The device as claimed in claim 3, wherein said polymeric material is a polyethylene, a polystyrene, a polyurethane, a polyvinyl acetate, a polyester, polyethylene terephthalate, an epoxy resin, a methacrylic polymer, a polycarbonate, a polyvinyl chloride, or a copolymer of said compounds.

40. The device as claimed in claim 3, wherein said polymeric material is a foil, preferably manufactured from polyester, polycarbonate, or polyvinyl chloride.

41. In a method of detecting and determining the concentration of at least one analyte in body fluids such as whole blood, plasma, serum, urine, secretion, cerebrospinal fluid, and from extracts of body tissues, and from swab material, the improvement comprising using the device of claim 1.

* * * * *